United States Patent [19]

Guo et al.

[11] Patent Number: 5,695,947
[45] Date of Patent: Dec. 9, 1997

[54] AMPEROMETRIC CHOLESTEROL BIOSENSOR

[75] Inventors: Dingli Guo, Union City; Paul Shieh, Fremont; Shek-Hong Lau, Fremont; Shu-Hui Chen, Fremont, all of Calif.

[73] Assignee: Biomedix, Inc., Fremont, Calif.

[21] Appl. No.: 471,026

[22] Filed: Jun. 6, 1995

[51] Int. Cl.$^6$ .............................. C12Q 1/60; G01N 27/26
[52] U.S. Cl. .............................. 435/11; 435/25; 435/817; 204/412
[58] Field of Search .................. 435/11, 25, 28, 435/817; 204/403, 412; 422/56, 57, 58

[56] References Cited

U.S. PATENT DOCUMENTS

| | | | |
|---|---|---|---|
| 4,973,549 | 11/1990 | Khanna | 435/11 |
| 5,108,564 | 4/1992 | Szuminsky | 204/153.12 |
| 5,225,064 | 7/1993 | Henkens et al. | 204/403 |
| 5,264,348 | 11/1993 | Schick et al. | 435/28 |
| 5,312,590 | 5/1994 | Gunasingham | 422/56 |
| 5,401,377 | 3/1995 | Shieh et al. | 204/418 |
| 5,501,956 | 3/1996 | Wada et al. | 435/11 |

OTHER PUBLICATIONS

Allen, et al, "Noninstrumented Quantitative Test System and Its Application for Determining Cholesterol Concentration in Whole Blood" Clinical Chemistry, vol. 36, No. 9, 1990.
Kajiya, et al, "Conferment of cholesterol sensitivity on polypyrrole films by immobilization of cholesterol oxidase and ferrocenecarboxylate ions" Journal of Electroanalytical Chemistry vol. 301, pp. 155–164, 1991.
Tatsuma, et al, "Oxidase/peroxidase bilayer-modified electrodes as sensors for lactate, pyruvate, cholesterol and uric acid" Analytica Chimica Acta, 242 (1991), pp. 85–89.
Crumbliss, et al, "A carrageenan hydrogel stabilized colloidal gold multi-enzyme biosensor electrode utilizing immobilized horseradish peroxidase and cholesterol oxidase/cholesterol esterase to detect cholesterol in serum and whole blood" Biosensors & Bioelectronics 8 (1993) 331–337.

Primary Examiner—Ralph Gitomer
Attorney, Agent, or Firm—Marvin S. Aronoff

[57] ABSTRACT

A sensor for the amperometric assay of cholesterol is provided which comprises a sensing electrode containing a first redox mediator and a reference electrode in simultaneous contact with a reagent strip containing a second redox mediator. The presence of the second redox mediator greatly amplifies the current flow produced by the presence of cholesterol and produces linear correlation of current flow with concentration over an extended range. The sensing electrode comprises a non-conductive support member having an electrically conductive layer containing the first redox mediator. The reference electrode is typically a Ag/AgCl electrode formed by coating an ink containing Ag/AgCl dispersed in a resin on a non-conductive base. The reagent strip is a porous or fibrous carrier, typically a paper, impregnated with a mixture containing the second redox mediator, cholesterol esterase, cholesterol oxidase, horseradish peroxidase, at least one surfactant and at least one stabilizer comprising an aqueous thickening agent. In one version of the sensor, the sensing electrode comprises a support member of polyester film coated with an electrically conductive graphite composition containing dimethylferrocene as the first redox mediator and the second redox mediator comprises 3,3',5,5'-tetramethylbenzidine. The sensor may be constructed in several physical forms. In one form, the sensing and reference electrodes are in the form of strips and the reagent strip is sandwiched between the electrically conductive layers of the electrodes with the reference electrode having a hole, through which the reagent strip is exposed, for the introduction of sample.

16 Claims, 5 Drawing Sheets

● TWO MEDIATORS: TMB/DMF    ● ONE MEDIATOR: DMF

AMPEROMETRIC CHOLESTEROL BIOSENSOR

BACKGROUND OF THE INVENTION

Knowledge of the cholesterol levels in human and animal blood, foodstuffs, and other complex mixtures has importance in medicine and industry. Determination of cholesterol in such complex mixtures is, however, often difficult and beset with time consuming and expensive sample preparation prior to the actual assay. At present, in medicine, blood samples are drawn from the patient and often sent to an off-site laboratory for blood cholesterol level determination. Currently, in the clinical laboratory setting spectrophotometric instrumentation using either absorption or reflectance of light is generally used to assay blood cholesterol levels. Such instrumentation is expensive and relatively complex to use. For example, daily calibration with manufacturer supplied standards are normally required and blood samples must be prepared before analysis. Typically a 5 ml sample of blood drawn from a patient is centrifuged and 50 µl samples of the supernatant liquid are used for each determination. The usual turnaround time in the clinical lab is at least 24 hours per analysis and the cost is relatively high. Desk top versions of such instrumentation suitable for use in the physician's office or the clinical lab are available but are relatively high priced and require calibration and sample preparation.

The medical practitioner and consequently, the patient must often wait days before the result of such an analysis is known, thus delaying the implementation of any needed corrective therapy.

Amperometric assay is another approach to the rapid assay of cholesterol in human or animal blood and other biological fluids. Such assays utilize sensing electrodes in conjunction with a single redox mediator and a combination of oxidative and hydrolytic enzymes.

For example, Crumbliss et al (Biosensors & Bioelectronics vol. 8, pg 331, 1993) utilized immobilized horseradish peroxidase on colloidal gold deposited on glassy carbon along with cholesterol oxidase/cholesterol esterase entrapped in carrageenan hydrogel as the sensing electrode. The redox mediator was either ferrocene or ferrocenecarboxylic acid deposited on the glassy carbon surface. The reference electrode was a silver wire. The linear detection range was 0–9 mg/dl and the response current was 6.6 µA/cm$^2$. Serum or whole blood samples required dilutions of 1:25 to 1:100 prior to cholesterol assay.

Tatsuma et al (Analytics Chimica Acta vol. 242, pg 85, 1991) assayed cholesterol with a sensor that employed a sensing electrode in which horseradish peroxidase and cholesterol oxidase were immobilized as a bilayer on tin (IV) oxide plate. The reference electrode was silver/silver chloride. Ferrocene monocarboxylic acid in a 0.1M, pH 5.9 citrate buffer was used as the redox mediator. The linear detection range of this sensor was 1–7 mmole/liter with a maximum response of only 20 nA/cm$^2$.

Kajiya et al (Journal of Electroanalytical Chemistry vol. 301, pg 155, 1991) fabricated a sensing electrode with cholesterol oxidase and cholesterol esterase in polypyrrole film with ferrocenecarboxylate as the electron mediator. A standard calomel electrode reference electrode was used. This cholesterol sensor yielded a maximum response current of 400 nA/cm$^2$ with a linear detection range of only 0–0.5 mmole/liter.

All of the above single redox mediator systems suffer from poor sensitivity and a narrow range of linear response restricted to low cholesterol concentrations. With such amperometric assay systems the usable linear range of detection falls below physiological concentrations of cholesterol in human blood serum. It should be noted that in terms of general guidelines for human serum cholesterol concentrations, a concentration less than 200 mg/dl (or about 5 mmole/liter) is considered desirable, while a blood serum concentration of about 200–240 mg/dl (or about 5–6 mmole/liter) is considered a moderate risk and a blood serum concentration greater than 240 mg/dl (or 6 mmole/liter) is considered a high risk. Consequently, sample dilution is generally mandatory for these methods.

For the foregoing reasons there is a need for a device for the quantitative assay of cholesterol in complex biological fluids such as blood and other complex mixtures such as foodstuff's, which is simple and convenient to use, delivers the assay rapidly, is highly sensitive, accurate and reproducible, requires little sample preparation, can be easily miniaturized; is inexpensive to produce and to use. In addition to the needs discussed above, there is a further need to increase the convenience and rapidity of cholesterol assays so they may be conducted in the setting of a physician's office, at the time of the patients visit, and on a routine basis at the patient's bedside in a hospital setting, or at home so that patient anxiety may be reduced and so that therapeutic programs may be initiated immediately.

BRIEF DESCRIPTION OF THE INVENTION

The present invention is directed to meeting the foregoing needs by providing a bi-redox mediator based amperometric cholesterol biosensor, which has high sensitivity and a wide range of linearity, for the direct and rapid measurement of free and total cholesterol in biological fluids such as serum, plasma or whole blood and in foodstuff preparations, without sample dilution. The cholesterol biosensor generally comprises a sensing electrode having a redox mediator dispersed in an electrically conductive medium such as an electrically conductive graphite formulation; a reference electrode such as a standard silver—silver chloride (Ag/AgCl) or calomel electrode; and a reagent strip containing reagents and enzymes with the membrane reagent strip in simultaneous contact with the electrically conductive medium having the redox mediator dispersed therein and the reference electrode. The reagent strip contains a second redox mediator system, cholesterol esterase, cholesterol oxidase and horseradish peroxidase in a gel medium. The electrically conductive medium of the sensing electrode contains a redox mediator such as dimethylferrocene (DMF), 7,7,8,8-Tetracyanoquinodimethane (TCNQ), Tetrathiafulvalene (TTF), Nickelocene (Nc), N-methylacridnium (NMA$^+$), Tetrathiatetracene (TTT), N-methylphenazinium (NMP$^+$) or mixtures thereof. The second redox mediator contained in the reagent strip may comprise a) various dyes and mixtures such as 4-aminoantipyrine (AAP), 3,3',5,5'-tetramethylbenzidine (TMB), 2,2'-azino-di-[3-ethyl-benzthiazoline sulfonate]; o-dianisidine, o-toluidine, benzidine, or b) various redox compounds, ions and complexes such as CN$^-$, Fe(CN)$_6^{-4}$, I$^-$, Co(NH$_3$)$_6^{++}$, Sn$^{++}$, S$^{-2}$ or Tl$^+$.

The sensor may be constructed in several physical forms. For example, both the sensing electrode and the reference electrode may be formed as coatings on separate non-conductive strips such as polyester film strips with these strips arranged so that they form a sandwich with the membrane reagent strip sandwiched between the two electrode strips and in simultaneous contact with the active, electrically conductive, surfaces of the electrode strips.

When the sensor is constructed in the sandwich configuration an opening is created in one or both of the electrode strips so that the reagent strip is exposed, enabling test samples to be placed on the reagent strip.

In another form, the separate strips on which the sensing and reference electrodes were formed are arranged side-by-side with a small separation between the strips, and the membrane reagent strip placed so that it forms a bridge between the two electrodes and is in simultaneous contact with the active, electrically conductive, surfaces of the sensing and reference electrodes.

In yet another form, both the sensing electrode and the reference electrode are formed on a common non-conductive support with a gap separating them. The reagent strip is then placed so that it forms a bridge between the two electrodes and is in simultaneous contact with the active, electrically conductive, surfaces of the sensing and reference electrodes. In this configuration a non-conductive protective cover such as a non-conductive film having an opening through which sample may be introduced may be placed over the reagent strip.

The cholesterol biosensor of the present invention, is especially useful where cholesterol must be assayed in complex mixtures such as in human or animal medicine for monitoring blood cholesterol levels and in the food industry, for monitoring cholesterol levels in foodstuffs. It has the further advantages of being easily miniaturized, being easy to use, using small test samples without extensive sample preparation and producing reliable results rapidly.

DESCRIPTION OF THE PREFERRED EMBODIMENTS

Figure 1A:
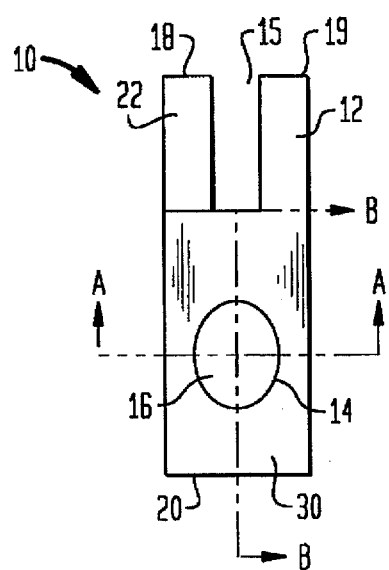
FIG. 1A is a top view of a sandwich version of a cholesterol sensor of the present invention.
Figure 1B:
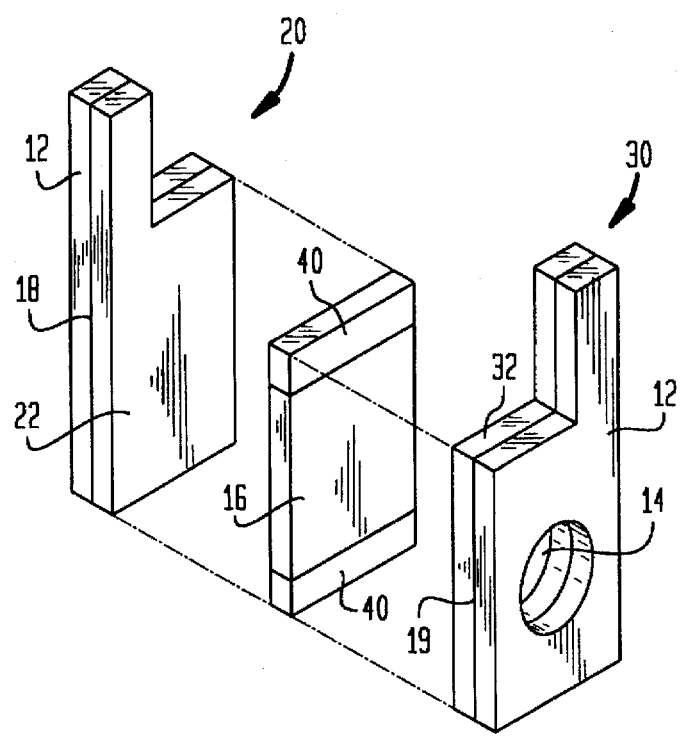
FIG. 1B is an exploded view of the version of the cholesterol sensor of FIG. 1A.
Figure 1C:
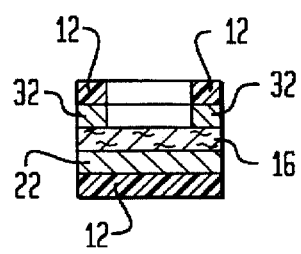
FIG. 1C is a cross-sectional view along the line A—A of FIG. 1A.
Figure 1D:
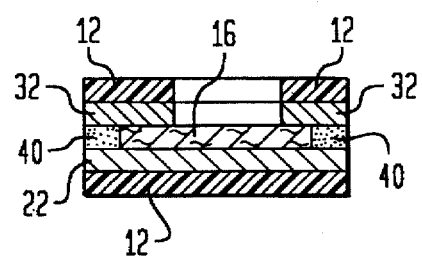
FIG. 1D is a cross-sectional view along the line B—B of FIG. 1A.

FIG. 1A, is a top view, FIG. 1B is an exploded view of FIG. 1A, FIG. 1C is a cross-sectional view along line A—A of FIG. 1A and FIG. 1D is a cross-sectional view along line B—B of FIG. 1A of a cholesterol biosensor 10 which is an embodiment of the present invention. The cholesterol biosensor 10 generally comprises a sensing electrode 20, a reference electrode 30 and a reagent strip 16. In the version of the sensor depicted in FIGS. 1A–1D, the sensing electrode 20 has a conductive protrusion 18 and reference electrode 30 has a conductive protrusion 19 separated by gap 15. Protrusions 18 and 19 serve as convenient points for electrical connection. Reagent strip 16 is sandwiched between sensing electrode 20 and reference electrode 30 and is in simultaneous contact with the electrically conductive layer 22 of sensing electrode 20 and the electrically conductive layer 32 of reference electrode 30. The sandwich configuration may be optionally held together by clamps, tape and the like. Optionally, spacers 40 may be used to keep sensing electrode 20 and reference electrode 30 physically separated. Spacers 40 may comprise any non-conductive adhesive means, such as adhesives and double sided adhesive tape.

Sensing electrode 20 comprises a non-conductive support member 12 for electrically conductive layer 22. The non-conductive support member may typically be any cohesive non-conductor such as any non-conductive film or street forming polymeric material, ceramics, glass, paper, cardboard. The preferred thickness of the non-conductive support material is from about 5 mil to about 10 mil. Polymeric materials, particularly non-conductive polymerics in the form of films or thin sheets are preferred as they may be readily cut to strips of suitable size. In practice non-conductive support 12 is a polymeric film or sheet. Any non-conductive polymeric film or sheet such as polyvinylchloride, polyester, polycarbonate, vinyl acetate copolymer, nylon, poly(1,4-butyleneterephthalate), cellulose propionate, ethylene/acrylic acid copolymer, polybutadiene, polyethylene, polypropylene, polyimide, acrylic film, polyurethane, polystyrene, and polyvinylfluoride may be used. Polyester film such as Mylar® is preferred as it is readily available and easily handled.

Electrically conductive layer 22 of sensing electrode 20 comprises an electrically conductive layer containing a redox mediator. Electrically conductive layer 22 may be formed from formulations of electrically conductive graphite or carbon and polymeric substances. Formulations of electrically conductive carbon or graphite containing polymeric materials such as the electrically conductive inks available from Ercon Inc. (Waltham Mass.) are preferred as they are readily available, can be uniformly spread on a non-conductive support member 12 to form a thin layer and can be easily blended with a redox mediator. Redox mediators which may be blended with electrically conductive formulations based on electrically conductive inks include dimethyl ferrocene (DMF), 7,7,8,8-tetracyanoquinodimethane (TCNQ), tetrathiafulvalene (TTF), Nickelocene (Nc), N-methylacridinium (NMA$^+$), Tetrathiatetracene (TTT), N-methylphenazinium (NMP$^+$), and mixtures thereof. DMF is preferred as it gives an easily detectable current change with change of cholesterol concentration when used in conjunction with a second redox mediator in the reagent strip 16. The preferred concentration of the redox mediator in the electrically conductive layer 22, based on the total weight of the dry electrically conductive layer 22, ranges from about 0.2% to about 15% with concentrations of about 0.5% to about 7% most preferred. Example 1a illustrates a process for making an embodiment of sensing electrode 20.

Reference electrode 30 comprises a non-conductive support member 12 for electrically conductive layer 32. The non-conductive support member may typically be may cohesive non-conductor such as any non-conductive film or sheet forming polymeric material, ceramics, glass, paper, cardboard. The preferred thickness of the non-conductive support material is from about 5 mil to about 10 mil. Polymeric materials, particularly non-electrically conductive polymerics in the form of films or thin sheets are preferred as they may be readily cut to strips of suitable size. In practice, non-conductive support 12 is a polymeric film or sheet. Any non-conductive polymeric film or sheet such as those used for the sensing electrode may be used. Polyester film such as Mylar® is preferred as it is readily available and easily handled.

Electrically conductive layer 32 of reference electrode 30 comprises a Ag/AgCl reference electrode prepared by coating a base support such as polyester film with an electrically conductive formulation comprising Ag/AgCl dispersed in a resin formulation, such as ERCON R-421(DBE-60) Silver/Silver Chloride and cutting the coating for about one hour at about 70° C. Other forms of reference electrodes may be used such as the Ag/AgCl reference electrodes described in U.S. Pat. No. 5,401,377, which is herein incorporated by reference to the extent that it is pertinent, however, Ag/AgCl electrodes based on Ag/AgCl electrically conductive formulations which may be conveniently spread on a non-conductive base are preferred. Example 1b illustrates a process lot making an embodiment of reference electrode 30.

Reagent strip 16 comprises a porous or fibrous water absorbent carrier impregnated with a reagent formulation. The carrier may be any water absorbent, porous medium including films, non-woven fabrics, felts, cellulosic papers, non-cellulosic papers, papers based on mixtures of cellulosic and non-cellulosic fibers or any water absorbent fibrous matrix, but commercially available cellulosic and non-cellulosic papers such as Baxter S/P qualitative filter paper grade 360, Brawny® paper (2-ply paper towel produced by James River Corp., Norwalk, Conn.), Leukosorb A mad B polyester paper (Pall Corp., Glen Cove, N.Y.), Whatman filter paper Numbers 1, 3, 4 and 114, Teri-plus™ 4-ply and KimTowel™ (Kimberly-Clark, Koswell, Ga.) are preferred as they have an adequate degree of absorbency for the reagent formulation, and are effective in hindering interference by particulate matter, such as formed bodies found in whole blood, with the cholesterol assay.

The reagent formulation contained in reagent strip 16 comprises a second compound or mixture of compounds that can function as a second redox mediator in addition to the first redox mediator which is contained in the sensing electrode, an enzyme mixture, surfactants, and stabilizers. Compounds and mixtures of compounds which can function as the second redox mediator include 4-aminoantipyrine (AAP), 3,3',5,5'-tetramethylbenzidine (TMB), 2,2'-azino-di-[3-ethyl-benzthiazoline sulfonate] (ABTS), o-dianisidine, o-toluidine, benzidine, $CN^-$, $Fe(CN)_6^{-4}$, $I^-$, $Co(NH_3)_6^{++}$, $Sn^{++}$, $S^{-2}$ or $Tl^+$. AAP and TMB are preferred as they generally produce relatively large changes in current flow with change of cholesterol concentration over a wide concentration range. The weight of the second redox mediator in reagent strip 16 ranges from about 0.001 mg to about 10 mg per sensor with the preferred weight range from about 0.001 mg to about 1 mg per sensor, and the most preferred weight range from about 0.01 mg to about 0.5 mg per sensor. The enzyme mixture comprises cholesterol esterase (CE), cholesterol oxidase (COX) and horseradish peroxidase (HP). The preferred quantity of CE ranges from about 0.5 IU to about 40 IU per sensor, with the most preferred quantity ranging from about 1 IU to about 15 IU per sensor. The preferred quantity of COX ranges from about 0.5 IU to about 80 IU per sensor, with the most preferred quantity ranging from about 1 IU to about 25 IU per sensor. The preferred quantity of HP ranges from about 0.5 IU to about 100 IU per sensor, with the most preferred quantity ranging from about 1 IU to about 15 IU per sensor.

The surfactants used in reagent strip 16 comprise Mega 8 (Octanoyl-N-methylglucamide), (Aldrich Chemical, Co. Milwaukee, Wisc.), cholic acid, salts of cholic acid, Triton X-100, polyethylene glycol, sodium lauryl sarcosinate and sodium lauryl sulfate used either separately or in combination. The preferred weight of surfactant ranges from about 0.1 mg to about 100 mg per sensor, with the most preferred weight ranging from about 1 mg to about 25 mg per sensor.

Any water soluble or water dispersible aqueous thickening or gelling agent may be used as a stabilizer in reagent strip 16 providing it does not interfere with the chemical processes which occur during the cholesterol assay. Preferred stabilizers include used separately or in combination. The preferred weight of any stabilizer ranges from about 0.01 mg to about 120 mg per sensor, with fie most preferred weight ranging from about 0.05 mg to about 30 mg per sensor. Example 1c illustrates a process for making an embodiment of reagent strip 16.

Embodiments of the cholesterol sensor may have different physical forms. Example 1d illustrates construction of a sensor having electrodes 20 and 30 and reagent strip 16 in a sandwich configuration, a version of which is illustrated in FIGS. 1A-1D.

In another physical form of the cholesterol biosensor, electrode strips 20 and 30 may be placed in a side-by-side configuration with a small separation between the strips, and the membrane reagent strip placed so that it forms a bridge between the two electrodes and is in simultaneous contact with the active, electrically conductive, surfaces of the sensing and reference electrode.

Figure 1E:
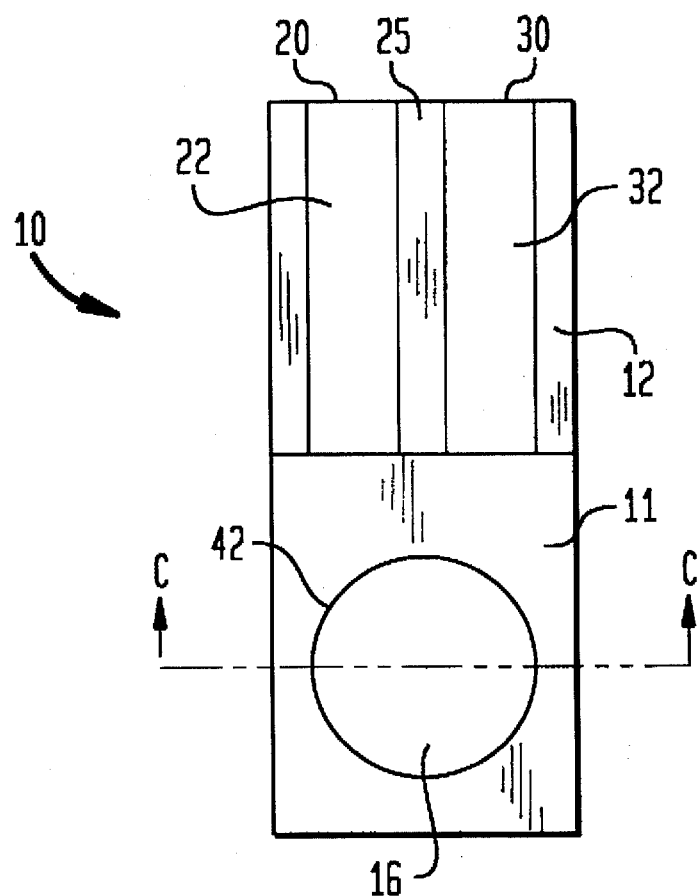
FIG. 1E is a top view of a side-by-side version of a cholesterol sensor of the present invention.
Figure 1F:
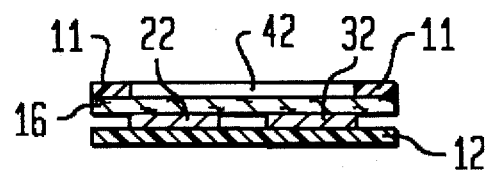
FIG. 1F is a cross-sectional view along the line C—C of FIG. 1E.

In yet another physical form, illustrated in FIG. 1B and FIG. 1F, sensing electrode 20, which comprises conductive layer 22, containing a first redox mediator, and reference electrode 30 which comprises layer 32 of an electrically conductive formulation comprising Ag/AgCl dispersed in a resin formulation, are laid down as adjacent strips on a common non-conductive support 12, with a gap 25, separating them. Gap 25 is generally about 0.5 mm–5 mm in diameter, with a gap of about 1 mm to about 2 mm preferred as the separation between conductive strips 22 and 32, since this produces sensors with good response. The reagent strip 16 is placed so that it forms a bridge between the two electrodes and is in simultaneous contact with the active surfaces of the sensing and reference electrode. Non-conductive protective cover 11, having opening 42, to expose reagent strip 16 for introduction of test samples, may be optionally placed over the reagent strip 16. Protective cover 11 is preferably made of a non-conductive film such as that used for non-conductive support 12.

Many other physical forms of the cholesterol biosensor are possible in which electrodes of different geometries and forms are used. The side-by-side arrangement using electrodes 20 and 30 formed on a common base, as illustrated in FIGS. 1E and 1F is preferred as a working sensor may be quickly and easily assembled in this arrangement. The sandwich configuration of flat strip electrodes 20 and 30 and reagent strip 16 is more preferred for its shorter distance between electrode surfaces and enhanced sensitivity.

The embodiments of the invention and their use are further illustrated by way of the following examples.

EXAMPLE 1a

This example illustrates the construction of a sensing electrode of the present invention. An equal amount by weight of graphite ink (ERCON G-448(I) Graphite, Ercon Inc.) and electrically conductive graphite powder (Fisher Scientific Co., Pittsburg, Penna.) were mixed. This mixture was mixed with 10% DMF in toluene/alcohol 1/1 to attain a mixture with a dynamic viscosity of about $2 \times 10^4$ poise when frequency $\omega = 1$(radius/second). This mixture was laid down on a Mylar® film base support and spread with a steel doctor knife having a gap of about 0.5 to about 6 mil to produce an evenly distributed thin layer. The graphite coating was cured at about 40° C. for 90 minutes.

A similar procedure was used to prepare sensing electrodes from redox electrodes such as TCNQ, TTF and Ne.

EXAMPLE 1b

This example illustrates the general procedure for preparation of a reference electrode. A commercial polymer-based Ag/AgCl ink (Ercon, Inc.) was laid down on a Mylar® base support and spread with a steel doctor knife with a gap ranging from 0.5 mil to 6 mil to obtain an evenly distributed thin layer. Typically the thickness of the wet material was about 1 mil. The Ag/AgCl coating was cured in an oven at 70° C. for one hour.

EXAMPLE 1c

This example illustrates preparation of a membrane reagent strip using two dipping steps. A 42 mm×52 mm piece of absorbent paper such as Baxter S/P qualitative filter paper Grade 360 or Brawny 2 ply paper towel (James River Corp., Norwalk, Conn.) was immersed in 1 ml of an aqueous solution containing 5 mg TMB and 0.05 mg gelatin. Excess liquid was blotted off and the paper was dried at 40° C. for 15 minutes. The strip was then dipped into 1 ml of a phosphate buffer solution, having pH about 6.8, containing 0.05 mg gelatin, 15 mg cholic acid sodium salt hydrate, 96 units cholesterol esterase, 240 units cholesterol oxidase and 48 units horseradish peroxidase. Excess liquid was then blotted off and the paper was dried again at 40° C. for 15 minutes. After the drying process, the paper was then cut into 10 mm×12 mm strips.

EXAMPLE 1d

This example illustrates construction of a version of cholesterol sensor having a sandwich configuration using the elements prepared in Example 1a, b and e. A version of this configuration is shown in FIG. 1A through FIG. 1D. A hole 14 was punched out through a section of the reference electrode. Double sided adhesive tape (e.g. 3M #415 and 465; and ARCare® #7148, 7840 and 7841 (Adhesives Research Inc., Glen Rock, Penna.) was applied to the active surface of the reference electrode on both sides of the punched out hole. A piece of reagent strip prepared as in Example 1c was placed over the punched out hole between the two pieces of double sided tape. The sensing electrode was then placed over the reference electrode so that its active surface made contact with the reagent strip and pressed down, so that it adhered to the double faced tape, forming a sandwich, in which the active surfaces faced each other and the reagent strip was sandwiched between the active surfaces and was in physical contact with them. Electrical connections were made to each electrode which were connected to the setup schematically represented in FIG. 7. The cholesterol sample was applied to the reagent strip through the hole in the reference electrode.

EXAMPLE 2

Figure 4:
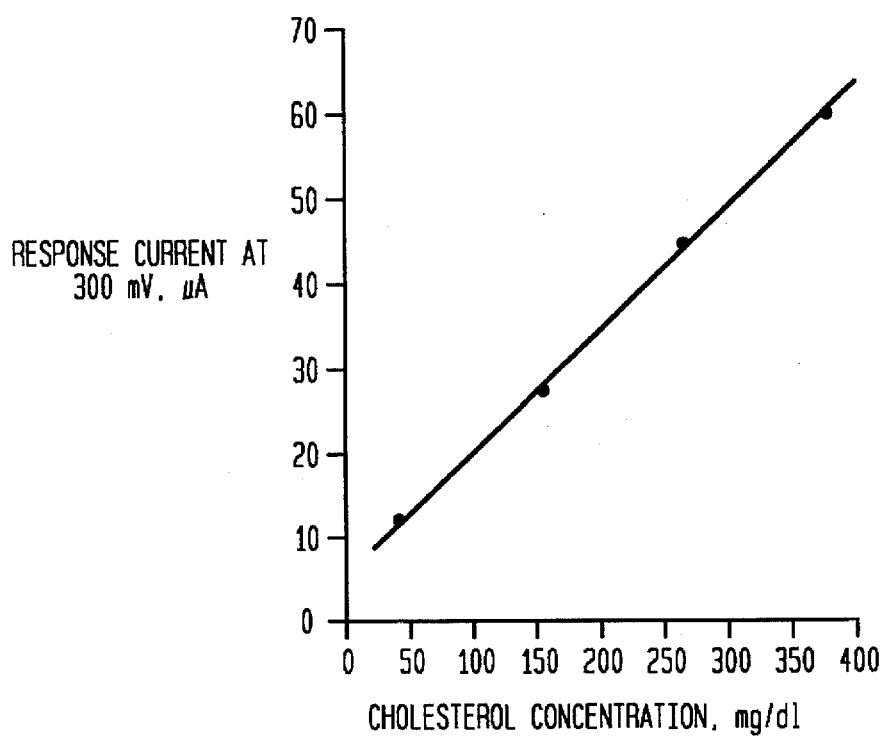
FIG. 4 shows a calibration curve of a version of a cholesterol sensor containing DMF in the sensing electrode and TMB in the reagent strip.
Figure 7:
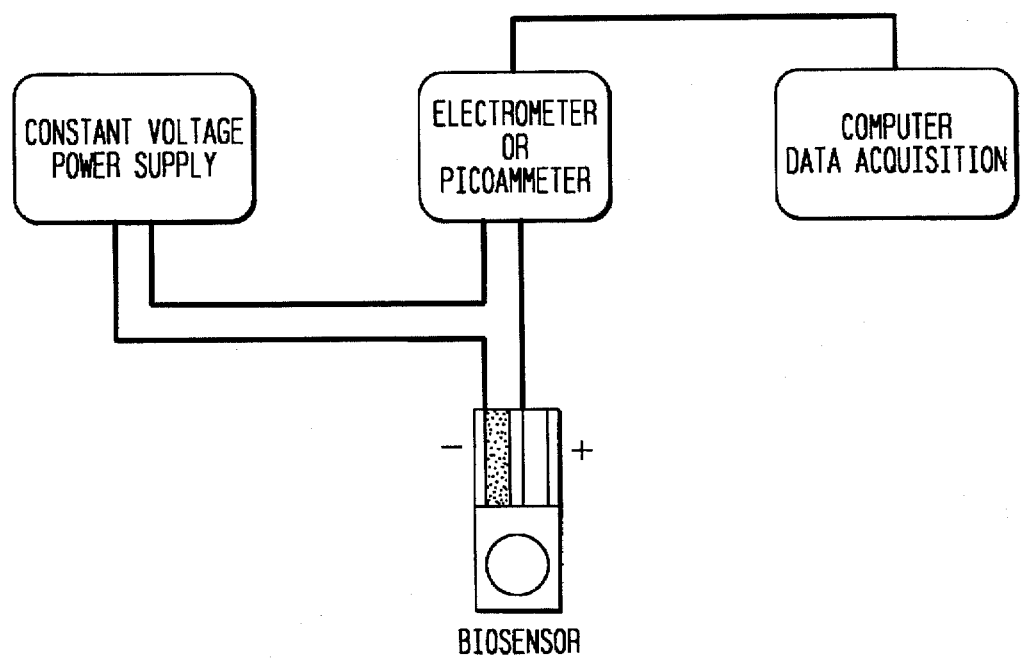
FIG. 7 is a schematic representation of a setup for cholesterol determination.

This example illustrates the determination of cholesterol concentration using a sensor having DMF in the sensing electrode (Example 1a), TMB in the reagent strip (Example 1c) and a strip Ag/AgCl reference electrode (Example 1b) having the sandwich configuration (Example 1d) and the setup schematically represented in FIG. 7. The response of the cholesterol samples was measured amperometrically under an applied constant potential of 300 mV from a constant power source. The response was recorded at relax intervals either manually or electronically by a data acquisition system via an IEEE 488 computer interface. Timing was initiated with the addition of a measured sample (about 20 μl) to the reagent strip. The current generated from the enzymatic redox reactions was detected by a picoammeter or an electrometer. Cholesterol concentrations of 40, 155, 270 and 385 mg/dl were measured within 1 minute using commercially available synthetic human serum standards from Verichem Lab Inc., Providence, R.I. The linear response obtained is depicted in FIG. 4. After calibration in this way, cholesterol concentration may be directly read on a meter.

EXAMPLE 3

Figure 3:
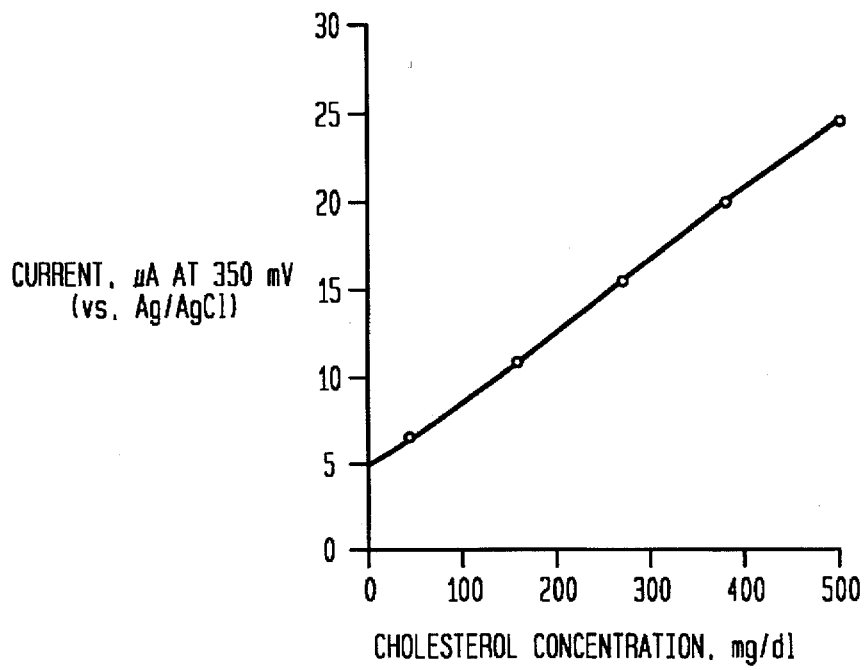
FIG. 3 shows a calibration curve of a version of a cholesterol sensor containing DMF in the sensing electrode and AAP in the reagent strip.

This example depicts the performance of another version of the cholesterol sensor using DMF in the sensing electrode, typically prepared as in Example 1a through 1d, except that AAP was used in the reagent strip instead of TMB. Cholesterol concentrations of 40, 155, 270, 385 and 500 mg/dl were measured within 3 minutes using commercially available synthetic human serum standards from Verichem Lab Inc., Providence, R.I. The linear response obtained is depicted in FIG. 3. After calibration in this way, cholesterol concentration may be directly read on a meter.

EXAMPLE 4

Figure 5:
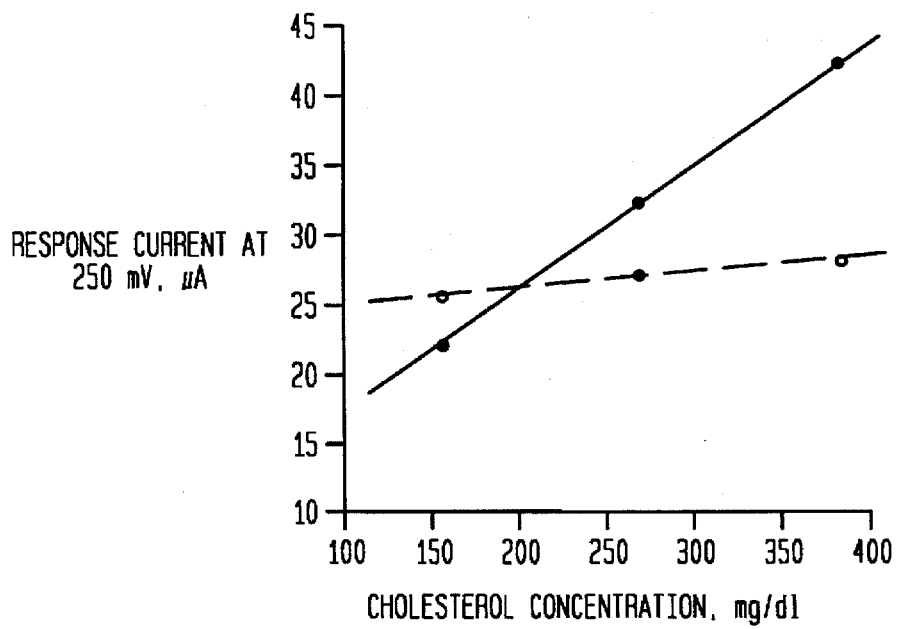
FIG. 5 shows a graph comparing the responses at different cholesterol concentrations of a cholesterol biosensor having 2 redox mediators to a cholesterol biosensor having 1 redox mediator.
Figure 6:
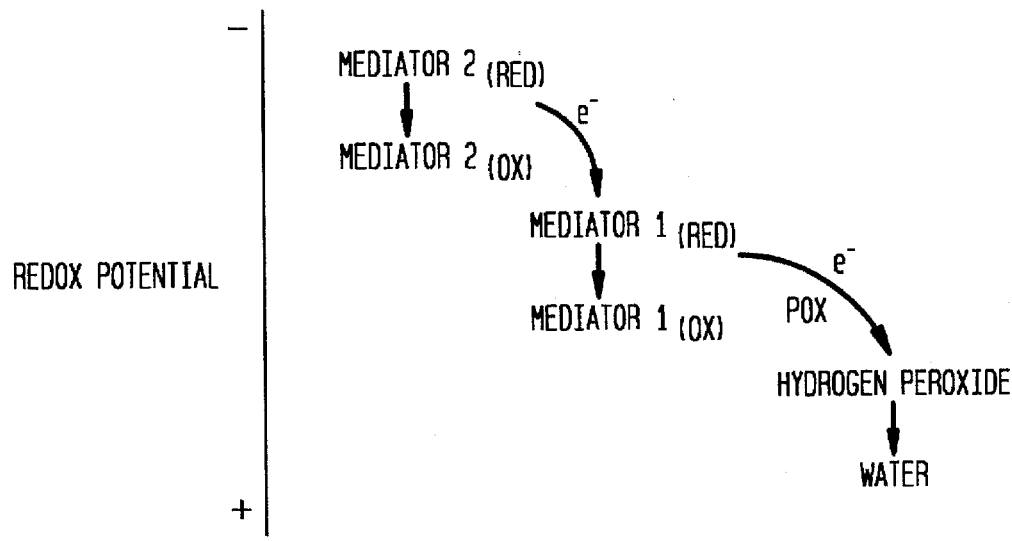
FIG. 6 is a redox process scheme for electron flow with 2 redox mediators.

This example shows the difference in response of a cholesterol biosensor using 2 redox mediators versus a cholesterol biosensor using only one redox mediator. The 2 mediator biosensor was prepared as in Examples 1a through 1d. The 1 mediator biosensor was prepared in the same way except that in preparing the reagent strip as described in Example 1e the TMB was omitted. Amperometric measurements at a constant applied potential of 250 mV were made on synthetic human serum standards (Verichem) having different cholesterol concentrations using each biosensor. These results are depicted in FIG. 5. It is seen that the 1 mediator system displays only a slight variation of response with change of cholesterol concentration, while the 2 mediator biosensor shows a large linear response with change of cholesterol concentration. The presence of the second redox mediator enhances the signal response. FIG. 6 is a depiction of a redox process scheme for electron flow from the second redox mediator which is found in reagent strip 16, to the first redox mediator which is found in electrically conductive layer 22 of sensing electrode 20, to hydrogen peroxide.

EXAMPLE 5

This example demonstrates the ability of a calibrated cholesterol sensor to accurately assay commercially available samples with known cholesterol content determined by other means. The version of the cholesterol biosensor having TMB in the reagent strip and DMF in the sensing electrode, prepared as in Examples 1a–1d, was calibrated with a commercially available cholesterol serum standard as in Example 2. A similar procedure was used to detect the currents produced by cholesterol containing serum samples from other sources. The currents generated by the samples from other sources were then converted to cholesterol concentrations using the calibration curve developed in Example 2. The results are given in Table 1. It is seen that the measured values of cholesterol concentrations using the bimediator cholesterol sensor are in good agreement with the stated values of these commercial standards.

TABLE 1

| SAMPLE SOURCE | STATED CHOLES- TEROL SAMPLE CONCENTRATION (MG/DL) | MEASURED CONCEN- TRATION USING TMB/ DMF BI-MEDIATOR SENSOR CALIBRATED AGAINST REFERENCE (VERICHEM, LEVELS A–E 40–500 MG/DL) |
|---|---|---|
| CIBA-CORNING, Gilford Systems Oberlin, OH 44074 | 159 | 153 |
| Level 1 Chol Calibrator, DuPont Wilmington, DE 19868 | 71 | 71 |
| Level 2 Chol Calibrator, DuPont Wilmington, DE 19868 | 227 | 220 |
| Level 3 Chol Calibrator, DuPont Wilmington, DE 19868 | 411 | 427 |

EXAMPLE 6

Figure 2:
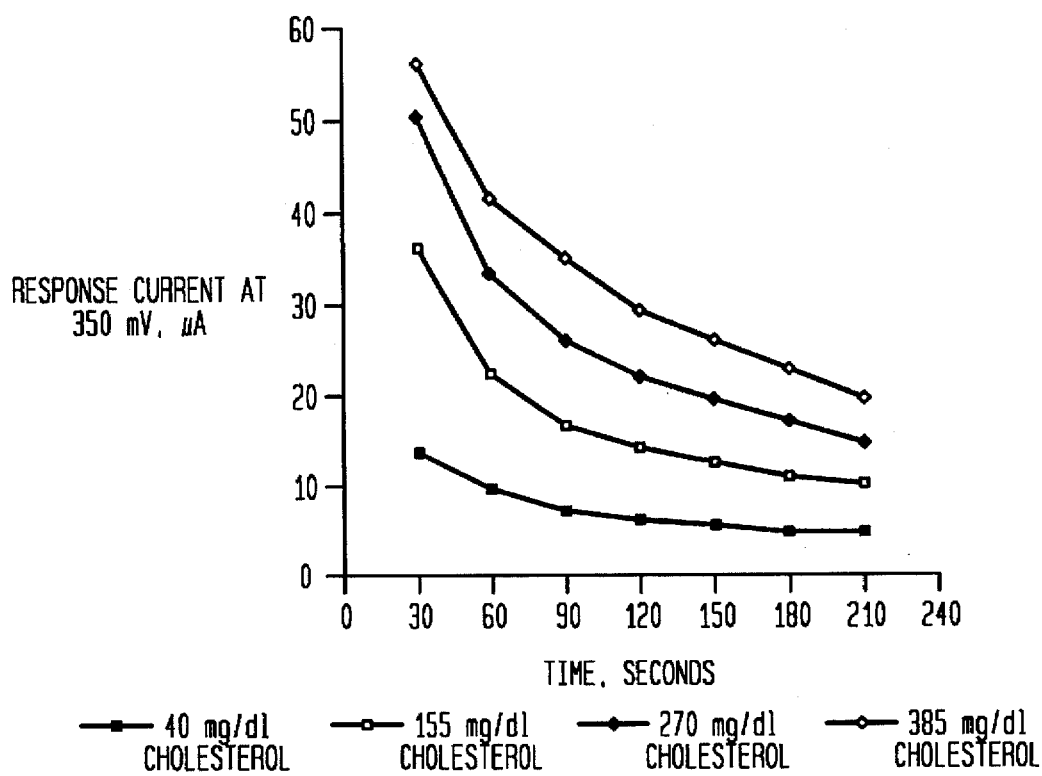
FIG. 2 shows a graph of response time versus response current at different cholesterol concentrations for a version of the cholesterol sensor containing DMF in the sensing electrode and AAP in the reagent strip.

This example illustrates the correlation of time vs current for samples having different cholesterol concentrations. These results were obtained with the version of the cholesterol biosensor described in Example 3, using AAP in the reagent strip and DMF in the sensing electrode. FIG. 2 gives the correlation of time vs current for measurements on synthetic human serum standards (Verichem) having cholesterol concentrations ranging from 40 to 385 mg/dl. For each concentration, linear current response was observed from about 1.5 to 3 minutes, FIG. 3 demonstrates the linearity and sensitivity range of the AAP system. Cholesterol serum concentrations ranged from 40 mg/dl to 500 mg/dl. In this concentration range, linearity of current response was achieved in 3 minutes.

The previously described versions of the present invention have many advantages, including ease and simplicity of preparation and use. The use of a second redox mediator expands the range of cholesterol concentrations which can be assayed and enhances the accuracy of detection by greatly magnifying the current flow produced compared to systems using a redox mediator only in the sensing electrode. After calibration, the cholesterol biosensor of the present invention allows direct readout of cholesterol concentration on a picoammeter or an electrometer. Other methods of cholesterol assay require manual determination of color migration followed by use of a table to determine the cholesterol level.

Cholesterol assays by versions of the present invention are rapid, taking 3 minutes or less. In addition, whole blood, serum or plasma may be used directly for cholesterol assay without sample treatment, thereby enabling cholesterol analysis to be conveniently performed in a physicians office or in a patients home.

Still another advantage of versions of cholesterol biosensors of the present invention is a high degree of stability giving them extended shelf life.

A further advantage of the cholesterol sensor of the present invention is that it operates at low applied potentials which minimizes the chance of interference from other redox reactions.

Yet another advantage of versions of the present invention is that since they can be made by a simple inexpensive process from low cost materials or very small quantities of more expensive materials, from an economic point of view, they may be disposed of after even a single use if this is desired.

Although the present invention has been described in considerable detail with reference to certain preferred versions thereof, other versions are possible. For example, other versions of the cholesterol biosensor are possible as is its use in conjunction with instrumentation such as devices for automatically assaying large numbers of samples. Versions of the cholesterol biosensor of the present invention may also comprise a portion of an analytical kit. Therefore, the spirit and scope of the appended claims should not be limited to the description of the preferred versions contained herein.

What is claimed is:

1. An amperometric cholesterol sensor comprising:
   a sensing electrode, the sensing electrode comprising;
      a non-conductive support member,
      the non-conductive support member coated with an electrically conductive graphite formulation, the electrically conductive graphite formulation containing,
         a first redox mediator,
            the first redox mediator selected from the group consisting of dimethyl ferrocene, 7,7,8,8-tetracyanoquinodimethane, tetrathiafulvalene, nickelocene, N-methylacridinium, tetrathiatetracene, N-methylphenazinium, and mixtures thereof, and
   a reference electrode, with the reference electrode and the sensing electrode having a gap between them, and
   a reagent strip, the reagent strip comprising;
      a water absorbent carrier, the water absorbent carrier impregnated with a mixture comprising;
         a second redox mediator,
            the second redox mediator selected from the group consisting of 4-aminoantipyrine, 3,3',5,5'-tetramethylbenzidine, 2,2'-azino-di-[3-ethylbenzthiazoline sulfonate], o-dianisidine, o-toluidine, benzidine, $CN^-$, $Fe(CN)_6^{-4}$, $I^-$, $Co(NH_3)_6^{++}$, $Sn^{++}$, $S^{-2}$, $Tl^+$ and mixtures thereof, and
         cholesterol esterase,
         cholesterol oxidase,
         horseradish peroxidase,
         at least one surfactant and,
         at least one stabilizer,
   with the electrically conducting graphite formulation of the sensing electrode and the reference electrode in simultaneous contact with the reagent strip, so that an electrical current can flow through the sensor.

2. The sensor of claim 1 in which the non-conductive support member of the sensing electrode comprises a polymeric film.

3. The sensor of claim 2 in which the reference electrode is a Ag/AgCl reference electrode comprising a non-conductive polymeric film support member coated with a layer of an electrically conductive formulation comprising Ag and AgCl dispersed in a resin formulation.

4. The sensor of claim 3 in which the water absorbent carrier comprising the reagent strip: comprises a fibrous matrix.

5. The sensor of claim 4 in which the fibrous matrix is selected from the group consisting of papers comprising cellulosic fibers, papers comprising non-cellulosic fibers and papers comprising mixtures of cellulosic and non-cellulosic fibers.

6. The sensor of claim 5 in which the surfactant is selected from the group consisting of Octanoyl-N-methylglucamide, cholic acid, salts of cholic acid, Triton X-100, polyethylene glycol, sodium lauryl sarcosinate, sodium lauryl sulfate and combinations thereof.

7. The sensor of claim 6 in which the stabilizer is selected from the group consisting of gelatin, sucrose, mannitol, poly(methylvinylether-co-maleic anhydride), gum arabic and combinations thereof.

8. An amperometric cholesterol sensor comprising:

a sensing electrode, the sensing electrode comprising;
  a non-conductive polymeric film, with the non-conductive polymeric film coated on one side with an electrically conductive formulation comprising a dispersion of electrically conductive graphite containing
    a first redox mediator,
      the first redox mediator selected from the group consisting of dimethyl ferrocene, 7,7,8,8-tetracyanoquinodimethane, tetrathiafulvalene, nickelocene, N-methylacridinium, tetrathiatetracene, N-methylphenazinium, and mixtures thereof, and a silver/silver chloride reference electrode comprising;
  a non-conductive polymeric film having an opening, the polymeric film coated on one side with an electrically conductive formulation comprising Ag/AgCl dispersed in a resin formulation, and a reagent strip, the reagent strip comprising;
  a water absorbent carrier, the carrier impregnated with
  a mixture comprising;
    a second redox mediator,
      the second redox mediator selected from the group consisting of 4-aminoantipyrine, 3,3',5,5'-tetramethylbenzidine, 2,2'-azino-di-[3-ethyl-benzthiazoline sulfonate], o-dianisidine, o-toluidine, benzidine, $CN^-$, $Fe(CN)_6^{-4}$, $I^-$, $Co(NH_3)_6^{++}$, $Sn^{++}$, $S^{-2}$, $Tl^+$ and mixtures thereof, and a
    mixture of enzymes, the mixture of enzymes comprising;
      cholesterol esterase,
      cholesterol oxidase,
      horseradish peroxidase,
    and, at least one surfactant,
    and at least one stabilizer, with the reagent strip sandwiched between, and in simultaneous physical contact with, the coated side of the sensing electrode and the coated side of the reference electrode, with the reagent strip exposed through the opening in the reference electrode.

9. The sensor of claim 8 in which the water absorbent carrier is a fibrous matrix.

10. The sensor of claim 9 in which the surfactant is selected from the group consisting of Octanoyl-N-methylglucamide, cholic acid, salts of cholic acid, Triton X-100, polyethylene glycol, sodium lauryl sarcosinate, sodium lauryl sulfate and combinations thereof.

11. The sensor of claim 10 in which the stabilizer is selected from the group consisting of gelatin, sucrose, mannitol, poly(methylvinylether-co-maleic anhydride), gum arabic and combinations thereof.

12. The sensor of claim 11 in which the first redox mediator is dimethylferrocene and the reagent strip is impregnated with the second redox mediator selected from the group consisting of 4-aminoantipyrine, 3,3',5,5'-tetramethylbenzidine, and $Fe(CN)_6^{-4}$; and the surfactant is cholic acid sodium salt hydrate; and the stabilizer is gelatin.

13. The sensor of claim 12 in which the sensing electrode further comprises a portion of the non-conductive polymeric film, coated on one side with the electrically conductive formulation containing the first redox mediator, that protrudes from the sensing electrode, with the portion that protrudes from the sensing electrode having no physical contact with the reagent strip, and the reference electrode further comprises a portion of the non-conductive film, coated on one side with the electrically conductive formulation comprising Ag/AgCl, that protrudes from the reference electrode, with the portion that protrudes from the reference electrode having no physical contact with the reagent strip and with the portion of the sensing electrode that protrudes from the sensing electrode and the portion of the reference electrode that protrudes from the reference electrode having a gap separating them.

14. The sensor of claim 13 further comprising at least one adhesive means adjacent to the reagent strip and sandwiched between the sensing electrode and the reference electrode, with the adhesive means simultaneously adhering to the coated side of the sensing electrode and the coated side of the reference electrode.

15. An amperometric sensing electrode, the sensing electrode comprising;

a non-conductive support member,
  the non-conductive support member coated with an electrically conductive graphite formulation, the electrically conductive graphite formulation containing,
    a redox mediator,
      the redox mediator selected from the group consisting of dimethyl ferrocene, 7,7,8,8-tetracyanoquinodimethane, tetrathiafulvalene, nickelocene, N-methylacridinium, tetrathiatetracene, N-methylphenazinium, and mixtures thereof.

16. The amperometric sensing electrode of claim 15 in which the non-conductive support member is a polymeric film.

* * * * *